(12) United States Patent
Salnik et al.

(10) Patent No.: US 7,002,690 B2
(45) Date of Patent: *Feb. 21, 2006

(54) ION IMPLANT MONITORING THROUGH MEASUREMENT OF MODULATED OPTICAL RESPONSE

(75) Inventors: Alex Salnik, Castro Valley, CA (US); Lena Nicolaides, Castro Valley, CA (US); Jon Opsal, Livermore, CA (US)

(73) Assignee: Therma-Wave, Inc., Fremont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/122,452

(22) Filed: May 5, 2005

(65) Prior Publication Data

US 2005/0190369 A1    Sep. 1, 2005

Related U.S. Application Data

(63) Continuation of application No. 10/387,259, filed on Mar. 12, 2003.

(60) Provisional application No. 60/378,140, filed on May 14, 2002, provisional application No. 60/365,237, filed on Mar. 18, 2002.

(51) Int. Cl.
*G01N 21/00* (2006.01)
*G01N 21/55* (2006.01)

(52) U.S. Cl. ..................... 356/432; 356/445

(58) Field of Classification Search ................. 356/432
See application file for complete search history.

(56) References Cited

U.S. PATENT DOCUMENTS

4,634,290 A    1/1987    Rosencwaig et al. .......... 374/5
4,636,088 A    1/1987    Rosencwaig et al. .......... 374/5

(Continued)

OTHER PUBLICATIONS

A. Ehlert et al., "Selected applications of photothermal and photoluminescence heterodyne techniques for process control in silicon wafer manufacturing," *Opt. Eng.*, vol. 36, No. 2, Feb. 1997, pp. 446-458.

S. Käpplinger et al., "Measurement of surface recombination of excess carriers by use of the double modulation technique," *Journal De Physique IV*, Colloque C7, supplément au Journal de Physique III, vol. 4, Jul. 1994, pp. C7-145-C7-149.

M. Hovinen et al., "Nondestructive analysis of ultrashallow junction implant damage by combined technology of thermal wave and spectroscopic methods," *J. Vac. Sci. Technol. B*, vol. 20, No. 1, Jan./Feb. 2002, pp. 431-435.

(Continued)

*Primary Examiner*—Hwa Andrew Lee
*Assistant Examiner*—Amanda Merlino
(74) *Attorney, Agent, or Firm*—Stallman & Pollock LLP

(57) ABSTRACT

A method for simultaneously monitoring ion implantation dose, damage and/or dopant depth profiles in ion-implanted semiconductors includes a calibration step where the photo-modulated reflectance of a known damage profile is identified in I-Q space. In a following measurement step, the photo-modulated reflectance of a subject is empirically measured to obtain in-phase and quadrature values. The in-phase and quadrature values are then compared, in I-Q space, to the known damage profile to characterize the damage profile of the subject.

16 Claims, 3 Drawing Sheets

U.S. PATENT DOCUMENTS

| | | | |
|---|---|---|---|
| 4,679,946 A | 7/1987 | Rosencwaig et al. | 374/5 |
| 4,854,710 A | 8/1989 | Opsal et al. | 356/432 |
| 5,074,669 A | 12/1991 | Opsal | 356/445 |
| 5,206,710 A | 4/1993 | Geiler et al. | 356/432 |
| 5,978,074 A | 11/1999 | Opsal et al. | 356/72 |
| 6,268,916 B1 | 7/2001 | Lee et al. | 356/369 |

OTHER PUBLICATIONS

L. Chen et al., "Characterizing Modulated Reflectance Signal from Ion-Implanted Silicon Wafers," *9th International Conference on PPP*, (China 1996), Digest, pp. 740-740.

A. Salnick et al., "Quantitative photothermal characterization of ion-implanted layers in Si," *Journal of Applied Physics*, vol. 91, No. 5, Mar. 1, 2002, pp. 2874-2882.

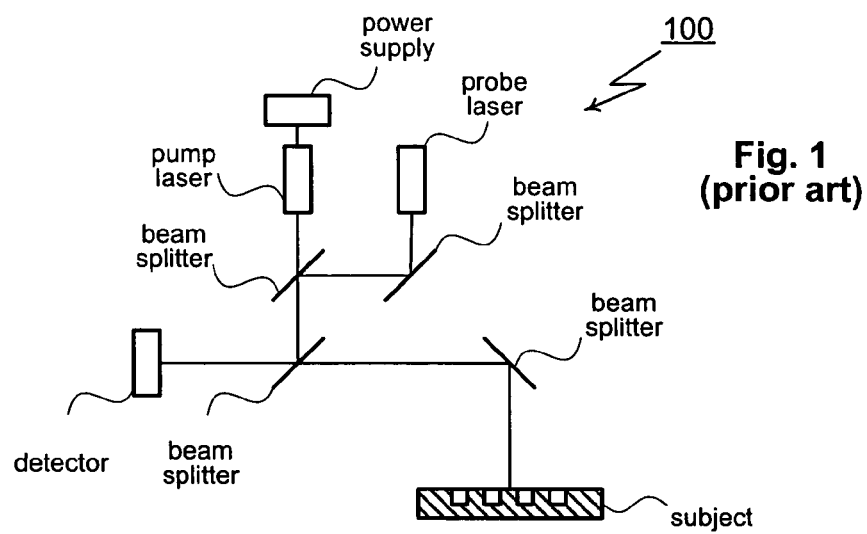
**Fig. 1
(prior art)**
**Fig. 2
(prior art)**
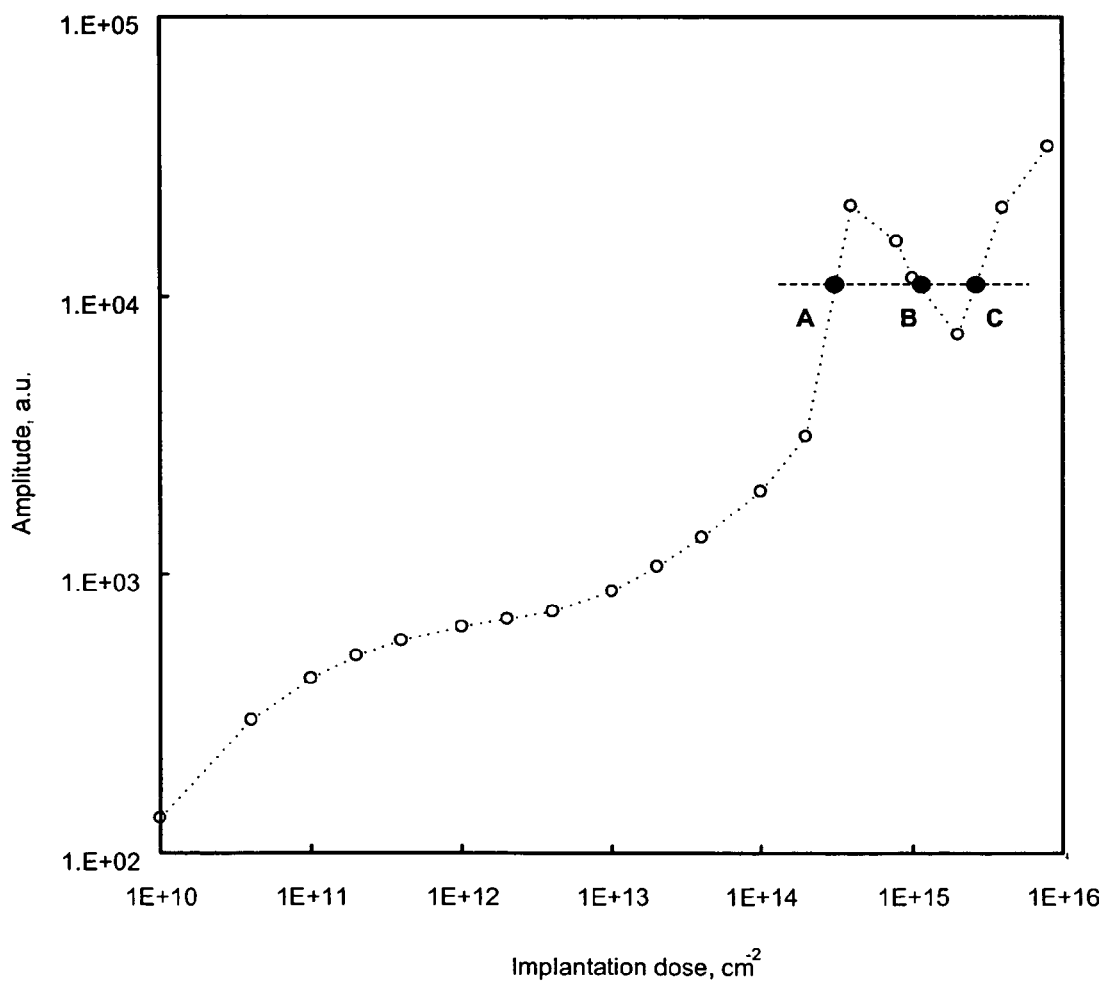

ION IMPLANT MONITORING THROUGH MEASUREMENT OF MODULATED OPTICAL RESPONSE

CLAIM OF PRIORITY

This application is a continuation of U.S. patent application Ser. No. 10/387,259, filed Mar. 12, 2003, which claims priority from U.S. Provisional Application Ser. No. 60/365,237, filed Mar. 18, 2002, and from U.S. Provisional Application Ser. No. 60/378,140, filed May 14, 2002, each of which is hereby incorporated herein by reference.

TECHNICAL FIELD OF THE INVENTION

The subject invention relates to optical devices used to non-destructively evaluate semiconductor wafers. In particular, the present invention relates to systems for measuring dopant concentrations in semiconductor samples.

BACKGROUND

As geometries continue to shrink, manufacturers have increasingly turned to optical techniques to perform non-destructive inspection and analysis of semiconductor wafers. The basis for these techniques is the notion that a subject may be examined by analyzing the reflected energy that results when an optical beam is directed at a subject. This type of inspection and analysis is known as optical metrology and is performed using a range of different optical techniques.

One widely used type of optical metrology system, as shown in FIG. 1, includes a pump laser. The pump laser is switched on and off to create an intensity-modulated pump beam. The pump beam is projected against the surface of a subject causing localized heating of the subject. As the pump laser is modulated, the localized heating (and subsequent cooling) creates a train of thermal and plasma waves within the subject. These waves reflect and scatter off various features and interact with various regions within the sample in a way that alters the flow of heat and/or plasma from the pump beam spot.

The presence of the thermal and plasma waves has a direct effect on the surface reflectivity of the sample. Features and regions below the sample surface that alter the passage of the thermal and plasma waves will therefore alter the optical reflective patterns at the surface of the sample. By monitoring the changes in reflectivity of the sample at the surface, information about characteristics below the surface can be investigated.

To monitor the surface changes, a probe beam is directed at a portion of the subject that is illuminated by the pump laser. A photodetector records the intensity of the reflected probe beam. The output signal from the photodetector is filtered to isolate the changes that are synchronous with the pump beam modulation. For most implementations, this is performed using a heterodyne or lock-in detector (See U.S. Pat. No. 5,978,074 and in particular FIG. 2 for a discussion of such a lock-in amplifier/detector). Devices of this type typically generate separate "in-phase" (I) and "quadrature" (Q) outputs. These outputs are then used to calculate amplitude and phase of the modulated signal using the following equations:

$$\text{Amplitude} = \sqrt{I^2 + Q^2} \quad (1)$$

$$\text{Phase} = \arctan(Q/I) \quad (2)$$

The amplitude and phase values are used to deduce physical characteristics of the sample. In most cases, this is done by measuring amplitude values (amplitude is used more commonly than phase) for one or more specially prepared calibration samples, each of which has known physical characteristics. The empirically derived values are used to associate known physical characteristics with corresponding amplitude values. Amplitude values obtained for test subjects can then be analyzed by comparison to the amplitude values obtained for the calibration samples.

Systems of the type shown in FIG. 1 (i.e., those using external means to induce thermal or plasma waves in the subject under study) are generally referred to as PMR (photomodulated reflectance) type systems. PMR-type systems are used to study a range of attributes, including material composition and layer thickness. PMR-type systems and their associated uses are described in more detail in U.S. patent Ser. Nos.: U.S. Pat. Nos. 4,634,290; 4,646,088; 4,679,946; 4,854,710; 5,854,719; 5,978,074; 5,074,669; and 6,452,685. Each of these patents is incorporate in this document by reference.

Another important use of PMR-type systems is measurement and analysis of the dopants added to semiconductor wafers. Dopants are ions that are implanted to semiconductors during a process known as ion implantation. The duration of the ion implantation process (i.e., total exposure of the semiconductor wafer) controls the resulting dopant concentration. The ion energy used during the implantation process controls the depth of implant. Both concentration and depth are critical factors that determine the overall effectiveness of the ion implantation process.

PMR-type systems are typically used to inspect wafers at the completion of the ion implantation process. The ion implantation damages the crystal lattice as incoming ions come to rest. This damage is typically proportional to the concentration and depth of ions within the crystal lattice. This makes measurement of damage an effective surrogate for direct measurement of dopant concentration and depth. PMR-type systems have proven to be adept at measuring damage and have been widely used for post implantation evaluation.

As shown in FIG. 2, the relationship between dopant concentration and amplitude measurements (i.e., as defined by Equation (1)) is monotonic for low dopant concentrations. As dopant concentrations increase (e.g., greater than 1E14 for $As^+$ or $P^+$ ions or greater than 1E15 for $B^+$ ions) the monotonic relationship breaks down. In fact, at high concentrations, the amplitude measurements are no longer well behaved and as a result cannot be used to accurately derive corresponding dopant concentrations. In FIG. 1, this is illustrated by the points A, B and C all having the same the same amplitude measurement, even though each point represents a different dopant concentration. The same sort of breakdown occurs as the type of implanted ions becomes heavier (e.g., $As^+$ or $P^+$ ions). In both cases, this is attributable to the appearance of a Si amorphous layer resulting in optical interference effects. Although not shown in FIG. 2, phase information becomes flat or insensitive to changes in concentration at high dopant concentrations or where heavy ions are implanted.

One approach for dealing with the problem of monitoring samples with high dopant concentrations is to measure the DC reflectivity of both the pump and probe beams in addition to the modulated optical reflectivity signal carried on the probe beam. Using the DC reflectivity data at two wavelengths, some ambiguities in the measurement can often be resolved. The details of this approach are described in U.S. Pat. No. 5,074,669 (incorporated in this document by reference).

In general, PMR-type systems of the type described above have proven to be effective methods for testing and characterizing semiconductor devices. Their ability to function in a non-contact, non-destructive fashion, combined with their high-accuracy and repeatability have ensured their widespread use as part of semiconductor manufacturing. Still, there is an obvious need for methods to provide this type of measurement capability for high dopant concentrations and ion implantation of relatively heavy ions.

BRIEF SUMMARY

The present invention provides a method of simultaneously monitoring ion implantation dose, damage and/or dopant depth profiles in ion-implanted semiconductors. For this method, a PMR-type optical metrology tool is used to record both quadrature (Q) and in-phase (I) values for a series of specially prepared calibration subjects. Each calibration subject is fabricated at the same implantation energy. As a result, variations recorded by the PMR-type system are largely attributable to variations in dopant concentration.

The measurement method performs a linear fit using the recorded points to define a calibration line within an I-Q plane. The slope of the calibration line is defined by the implantation energy used to create the calibration subject. Points along the calibration line correspond to different dopant concentrations. The calibration line is used to define a calibration region within the I-Q plane. The calibration region includes all points within a specified distance (often defined in terms of a percentage) of the calibration line. Typically, this is done by defining an upper boundary line that has a slightly greater slope than the calibration line and a lower boundary line that has a slightly smaller slope than the calibration line. The calibration region is the area between the upper and lower boundary lines.

After creating the calibration region, the PMR-type optical system may be used to inspect and analyze semiconductor wafers. For each subject wafer, the PMR-type system makes one or more measurements. Measurements that fall within the calibration region are known to share the damage profile of the calibration subject. Measurements that do not fall within this region are assumed to deviate from the known damage profile of the calibration subject. This test provides an effective method of accepting or rejecting wafers that provide acceptable accuracy even when dopant concentrations are high or where heavy ions have been implanted.

BRIEF DESCRIPTION OF THE DRAWINGS

FIG. 1 is a diagram of a photo-modulated reflectometer as used by the present invention.

FIG. 2 is a plot of amplitude measurements as a function of implant dose, from the sample output of the photo-modulated reflectometer of FIG. 1.

DETAILED DESCRIPTION

The present invention provides a method for simultaneously measuring ion implantation dose, damage and/or dopant depth profiles in ion-implanted semiconductors. The measurement method is logically divided into two steps: a calibration and a measurement step. During the calibration step, the photo-modulated reflectance of a known damage profile is characterized. Typically, this involves identifying one or more areas within I-Q space that correspond to the photo-modulated reflectance of the known damage profile. All other areas within I-Q space are then assumed to be dissimilar to the known damage profile. In the measurement step, I-Q measurements for a test subject are obtained empirically. The empirically obtained I-Q measurements are then compared to determine if they fall within an identified region of I-Q space. This comparison indicates whether the test subject has a damage profile that is similar to the known damage profile. The following sections describe several possible implementations for both the calibration and measurement steps.

Figure 3:
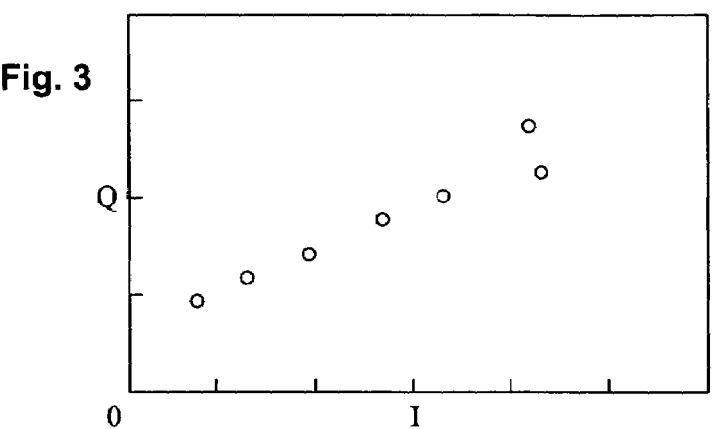
FIG. 3 is a plot of quadrature (Q) and in-phase (I) values recorded by the photo-modulated reflectometer of FIG. 1 for a series of subjects within a specially prepared calibration set.
Figure 4:
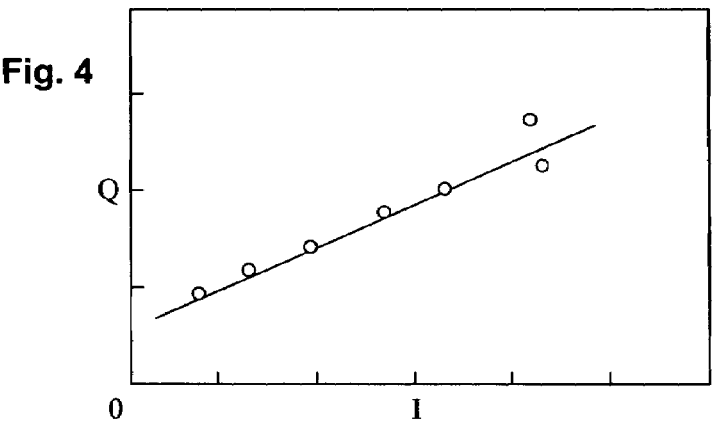
FIG. 4 shows a calibration line that best fits the I-Q points of FIG. 3.

For a first implementation of the calibration step, a PMR-type optical metrology tool is used to record both quadrature (Q) and in-phase (I) values for a series of specially prepared calibration subjects. Each calibration subject is fabricated at the same implantation energy. As a result, variations recorded by the PMR-type system are largely attributable to variations in dopant concentration. Each measured value is treated as a point within an I-Q plane. FIG. 3 shows a representative series of measured values plotted as points within an I-Q plane. The calibration step uses a linear fitting algorithm (such as least squares) to define a calibration line that best fits the points within the I-Q plane. FIG. 4 shows a calibration line that corresponds to the representative points of FIG. 3. The slope of the calibration line is defined by the implantation energy used to create the calibration subjects. Points along the calibration line correspond to different dopant concentrations.

Figure 5:
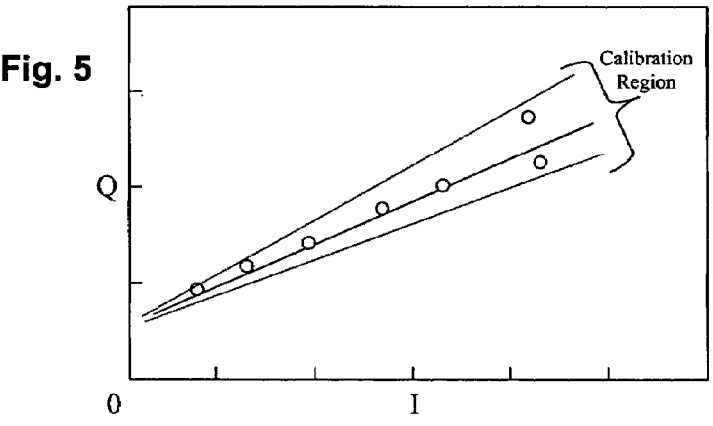
FIG. 5 shows a calibration region centered around the calibration line of FIG. 4.

The calibration line is used to define a calibration region within the I-Q plane. The calibration region includes all points within a specified distance (often defined in terms of a percentage) of the calibration line. As shown in FIG. 5, this is typically accomplished by defining an upper boundary line and a lower boundary line. The upper boundary line has a greater slope and the same Q-intercept as the calibration line. The lower boundary line has a smaller slope and the same Q-intercept as the calibration line. The calibration region is the area within the I and Q space that is bounded by the upper and lower boundary lines.

Figure 6:
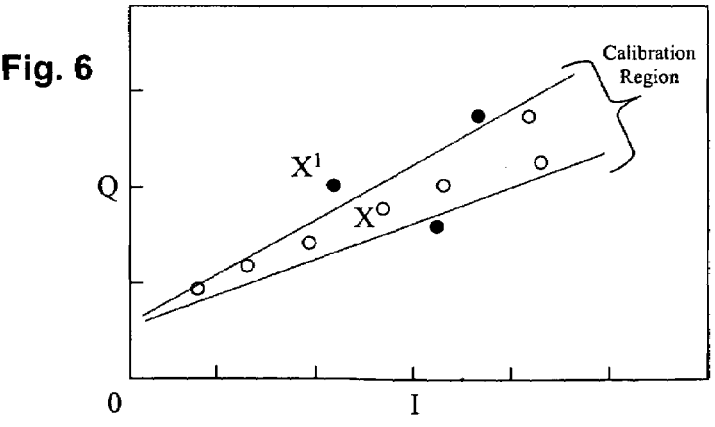
FIG. 6 shows the use of the calibration region of FIG. 5 to accept or reject measurements recorded by the photo-modulated reflectometer of FIG. 1.

For the associated measurement step, the PMR-type optical system is typically used to inspect and analyze a series of semiconductor wafers. For each subject wafer, the PMR-type system makes one or more measurements. Each measurement includes both I and Q values and defines a point within the I-Q plane. For the measurement method, the proximity of each point to the calibration line measures the similarity of that point to the damage profile of the calibration subject. Points that are close to the calibration line represent minor departures from the dopant depth and concentrations of the calibration subjects. Points that are further away represent larger departures. Points that fall outside of the calibration region (shown as black dots in FIG. 6) represent even larger departures from the calibration subject. These points are assumed to represent large deviations from the known damage profile of the calibration subject resulting from channeling effects, wafer/beam nonuniformities, etc. It should be noted that points that inside of the calibration region or even on the calibration line (such as point X) can be very similar in amplitude to points that fall outside of the calibration regions (such as point $X^1$). In a prior art system, that examines only amplitude, the difference between these two points would be undetectable. Similar ambiguities can also arise where points that have different amplitudes correspond, in fact, to the same damage profile. Prior art techniques would be unable to detect the similarity of such points.

Figures 7, 8:
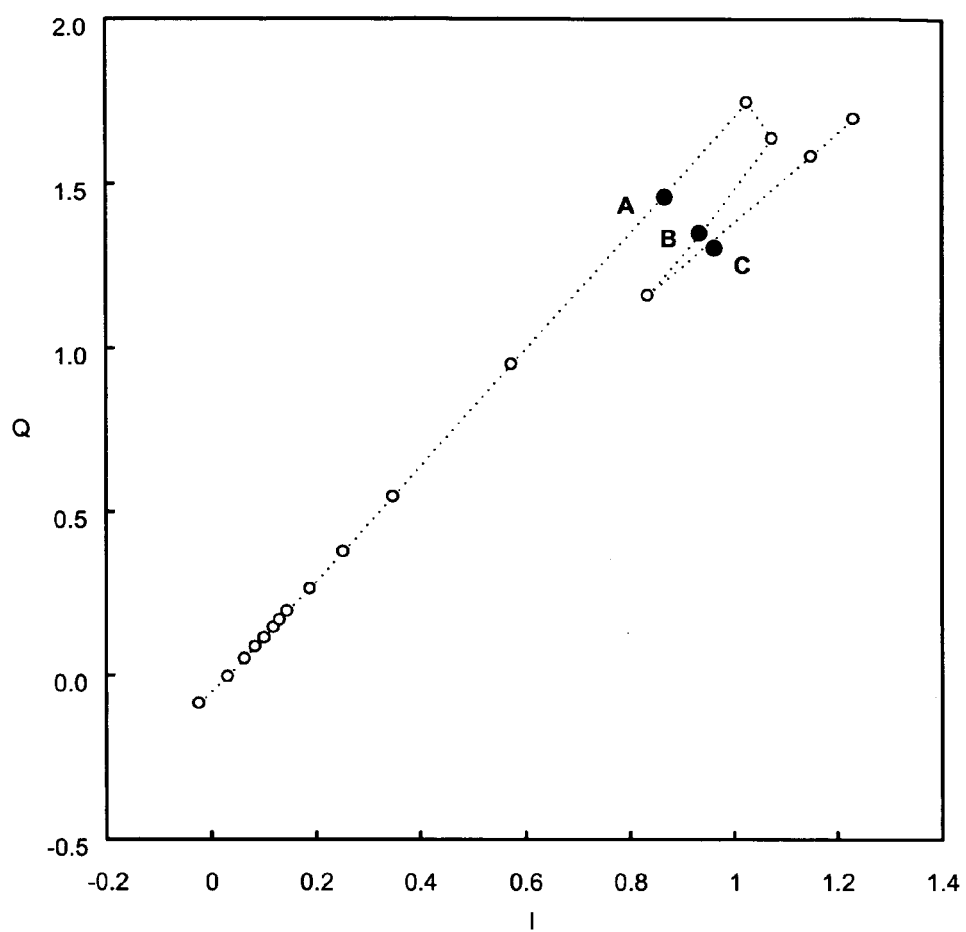
FIG. 7 is a second plot of quadrature (Q) and in-phase (I) values recorded by the photo-modulated reflectometer of FIG. 1 for a series of locations within a specially prepared calibration subject.
FIG. 8 shows a series of calibration lines that best fit the I-Q points of FIG. 7.

For a second implementation of the calibration step, a PMR-type optical metrology tool is again used to record both quadrature (Q) and in-phase (I) values for a series of specially prepared calibration subjects. A representative series of points of this type are shown in FIG. 7. As shown in FIG. 8, the calibration step uses these points to create a series of calibration lines. Each line is localized to fit a subset of the points measured by the PMR-type optical metrology tool. In this example, three calibration lines have been defined. The first is localized to fit the points that are local to point A. The second and third are localized to fit the points near point B and C, respectively. The slope of each calibration line reflects its associated implantation energy. Points along each line reflect different dopant concentrations.

For the associated measurement step, each point measured by the PMR-type optical metrology tool is compared to see if it lies on or near any of the calibration lines. Points on or nearby calibration lines share the damage profile of the associated calibration line. Points that are not near (or on) calibration lines represent major departures from the dopant depth and concentration of the calibration subjects due to channeling effects, wafer/beam nonuniformities, etc. It should be noted that points on different calibration lines (such as points A, B and C) can have identical amplitudes. Using prior art techniques that examine only amplitude, the difference between these points would be undetectable. Similar ambiguities can also arise where points that have different amplitudes correspond, in fact, to the same damage profile. Prior art techniques are unable to detect the similarity of such points.

The preceding description has focused on the use of in-phase (I) and quadrature (Q) signals. It is important to realize that there may be implementations that use linear combinations of these signals, in place of the I and Q values. This description and the following claims are specifically intended to cover all useful linear combinations of this type, without limitation.

It should be noted that this approach is useful in systems that measure the modulated reflectivity of the probe as well as systems that monitor other periodic surface variations such as in interferometry systems or periodic angular variations ("pump" type systems). To the extent these experiments are performed on semiconductor samples, it should also be understood that a portion of the signal would be the result of the modulated electron hole plasma as opposed to being a purely thermal signal. The relative contributions of the plasma and thermal effects on the signals depends on the dosage level and experimental conditions such as pump and probe beam wavelengths, beam spot size and pump modulation frequency.

It should also be noted that the measurement method is useful both as described, and as part of a more complex analysis. This means, for example that there may be cases where the measurement method will be used in combination with related measurements that analyze either or both of amplitude and phase information.

What is claimed is:

1. A method of optically inspecting and evaluating ion implantation in a subject, the method comprising:
    identifying calibration points within an I-Q space that correspond to the photo-modulated reflectance of known ion concentrations;
    making multiple photo-modulated reflectance measurements of the subject to obtain in-phase and quadrature values; and
    comparing the in-phase and quadrature values obtained from the subject to the calibration points to compare the ion concentrations of the subject to the known ion concentrations.

2. A method as recited in claim 1, wherein:
    at least some of the calibration points are identified empirically by analyzing the photo-modulated reflectance of a calibration subject.

3. A method as recited in claim 1, wherein:
    each of the multiple photo-modulated reflectance measurements includes the steps of:
        periodically exciting a region on the sample;
        directing a probe beam to reflect off the region on the sample surface that has been periodically excited;
        monitoring the reflected probe beam and generating an output signal in response thereto; and
        analyzing the output signal with a phase synchronous detection system and generating in-phase and quadrature signals.

4. A method as recited in claim 1, wherein:
    at least some of the calibration points are identified by extrapolating from empirically identified points.

5. A method as recited in claim 4, wherein:
    the process of extrapolation includes defining one or more calibration lines within I-Q space, each calibration line being a linear fit of a set of empirically identified points.

6. A method of evaluating ion concentration in a sample comprising the steps of:
    periodically exciting at least one region on the sample;
    directing a probe beam to reflect off each region on the sample surface that has been periodically excited;
    monitoring the reflected probe beam at each region and generating an output signal in response thereto;
    analyzing the output signal with a phase synchronous detection system and generating in-phase and quadrature signals; and
    evaluating the ion concentration of each region by comparing values of the in-phase versus the quadrature signals to predetermined reference values.

7. A method as recited in claim 6 that further comprises:
    evaluating the sample by comparing the value of either the amplitude or phase of the signals to predetermined reference values.

8. A method as recited in claim 6, wherein:
    the predetermined reference values are identified empirically by analyzing the photo-modulated reflectance of at least one calibration subject.

9. A method as recited in claim 6, wherein:

a linear combination of in-phase and quadrature signals is evaluated.

10. A device for evaluating ion concentration in a sample, the device comprising:

a first illumination source producing an intensity modulated beam for periodically exciting at least one region on the sample;

a second illumination source producing a probe beam to reflect off each region on the sample surface that has been periodically excited;

a detector for monitoring the reflected probe beam at each region and generating an output signal in response thereto;

a lock-in amplifier for analyzing the output signal to generate in-phase and quadrature signals; and a processor for evaluating ion concentration at each region by comparing values of the in-phase versus the quadrature signals to predetermined reference values.

11. A device as recited in claim 10, wherein:

the processor evaluates the sample by comparing the values of either the amplitude or phase of the signal to predetermined reference values.

12. A device as recited in claim 10, wherein:

the predetermined reference values are identified empirically by analyzing the photo-modulated reflectance of at least one calibration subject.

13. A device as recited in claim 10, wherein:

the processor evaluates a linear combination of in-phase and quadrature signals.

14. A method of evaluating variations in dopant concentration in a semiconductor sample, the method comprising:

directing an intensity modulated pump beam and a probe beam to the sample surface;

obtaining measurements by analyzing the reflected probe beam, each measurement composed of an in-phase (I) value and a quadrature (Q) value; and analyzing variations in dopant concentration for the semiconductor sample as a function of the I and Q values included in the measurements.

15. A method as recited in claim 14, further comprising:

comparing the variations in dopant concentration to previously derived calibration points associated with at least one calibration sample.

16. A method as recited in claim 14, wherein:

the I and Q values are compared to calibration I and Q values obtained from one or more calibration samples having known dopant concentration values.

* * * * *